US00PP19674P2

(12) United States Plant Patent
Hansen

(10) Patent No.: US PP19,674 P2
(45) Date of Patent: Feb. 3, 2009

(54) ***HOSTA* PLANT NAMED 'NEPTUNE'**

(50) Latin Name: *Hosta hybrid*
Varietal Denomination: Neptune

(75) Inventor: Hans Andrew Hansen, Waseca, MN (US)

(73) Assignee: Shady Oaks Nursery, LLC, Waseca, MN (US); Part Interest ( * ) Notice: Subject to any disclaimer, the term of this patent is extended or adjusted under 35 U.S.C. 154(b) by 0 days.

(21) Appl. No.: 12/005,842

(22) Filed: Dec. 28, 2007

(51) Int. Cl.
*A01H 5/00* (2006.01)

(52) U.S. Cl. ..... Plt./353
(58) Field of Classification Search ..... Plt./353
See application file for complete search history.

*Primary Examiner*—Annette H Para
*Assistant Examiner*—Louanne C Krawczewicz Myers
(74) *Attorney, Agent, or Firm*—Penny J. Aguirre

(57) ABSTRACT

A new cultivar of hybrid *Hosta* named 'Neptune', characterized by its ovate-shaped, blue-green leaves with undulating margins and an intense glaucous bloom on the lower surface. Its leaves cascade downward to form an upright, mounded habit with pale lavender flowers emerging on arching scapes in late summer.

1 Drawing Sheet

Botanical classification: *Hosta hybrida.*
Cultivar designation: 'Neptune'.

BACKGROUND OF THE INVENTION

The present invention, *Hosta* 'Neptune', relates to a new and distinct cultivar of *Hosta*, botanically known as a *Hosta hybrida,* and hereinafter will be referred to by its cultivar name 'Neptune'.

'Neptune' was selected in summer of 2004 and originated from a controlled cross, designated 99-371, made by the inventor in Waseca, Minn. in summer of 1999. The pod parent was an unnamed seedling of the inventor's, designated 97-316 (*Hosta* 'Maekawa'×'Halcyon') and the pollen parent was *Hosta* 'Salute'. The parent plants are not patented.

Asexual reproduction of the new cultivar was first accomplished by the inventor utilizing in vitro propagation in Waseca, Minn. in August of 2006. Asexual reproduction of the new cultivar by division and tissue culture has shown that the unique features of 'Neptune' are stable and reproduced true to type in successive generations.

SUMMARY OF THE INVENTION

The following traits have been repeatedly observed in trials in Minnesota for a period of seven years and represent the characteristics of the new cultivar. These attributes in combination distinguish 'Neptune' as a new and unique cultivar of *Hosta.*

1. 'Neptune' exhibits leaves that are ovate in shape with undulating margins.
2. The leaf color of 'Neptune' is blue-green with a surface that exhibits a glaucous bloom that is particularly intense on the lower surface (silvery-white in color).
3. The plant habit of 'Neptune' is an upright mound with leaves that cascade downward.
4. 'Neptune' reaches a height of about 60 cm (exclusive of flower scapes) and a spread of about 1.2 m in seven years.
5. 'Neptune' blooms in late summer with pale lavender flowers on arching flower scapes.

In comparison:
'Maekawa' differs from 'Neptune' in having wider, more heart-shaped leaves with margins that are less undulated. 'Halcyon' differs from 'Neptune' in having leaves that are more heart-shaped, thicker in substance, more blue in color, held more horizontally and in having leaf margins that are not undulated. 'Salute' differs from 'Neptune' in having leaves that are held upright rather than cascading and in leaf aspect as the margins of 'Salute' fold inward. In addition to the above parental plants, 'Neptune' can also be compared to 'Cutting Edge' (not patented). 'Cutting Edge' is similar to 'Neptune' in having wedge-shaped blue-green leaves with silvery lower surface and undulating margins, however 'Cutting Edge' is a smaller sized *Hosta* with smaller leaves, margins that curl inward and leaves that are held more horizontal.

BRIEF DESCRIPTION OF THE DRAWING

The accompanying colored photograph illustrates the distinct foliage characteristics of the new *Hosta.* The photograph was taken in June of a seven year-old plant of 'Neptune' as grown outdoors in Waseca, Minn. Colors in the photograph may differ slightly from the color values cited in the detailed botanical description which accurately describe the colors of the new *Hosta.*

DETAILED BOTANICAL DESCRIPTION OF THE PLANT

The following is a detailed description of a seven year-old plant of the new cultivar as grown outdoors in a trial garden in Waseca, Minn. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

General Description:

*Blooming period.*—About 4 weeks in late summer.

*Plant habit.*—Herbaceous perennial, clump-forming, upright mounded habit with cascading leaves.

*Height and spread.*—Reaches about 60 cm in height (excluding flower scapes) and about 1.2 m in width.
*Hardiness.*—U.S.D.A. Zones 3 to 8.
*Culture.*—Light to full shade, moist soils of moderate fertility.
*Diseases and pests.*—Average substance confers some resistance to slugs, no susceptibility or resistance to diseases or other pests has been observed.
*Root description.*—Freely branched, fleshy.
*Propagation.*—In vitro propagation is the preferred method utilizing typical methods for *Hosta,* division are also possible.
*Root development.*—Rooted transplants from tissue culture fully develop in a 96-cell liner in about 6 to 8 weeks in a greenhouse with average temperatures of about 70° F.
*Growth rate.*—Moderate.

Foliage Description:
*Leaf shape.*—Ovate.
*Leaf division.*—Simple.
*Leaf base.*—Broadly cuneate.
*Leaf apex.*—Acuminate.
*Leaf venation.*—Average of 9 pairs of veins, camptodrome pattern, impressed on upper surface and raised on lower surface, color upper surface (spring); mid rib 144B, laterals 144D, color lower surface (spring); mid rib 145C, laterals 144A.
*Leaf margins.*—Entire, wavy.
*Leaf attachment.*—Petiolate.
*Leaf arrangement.*—Basal, radiate spirally from base.
*Leaf surface.*—Slightly glaucous on upper surface and highly glaucous on lower surface.
*Leaf substance.*—Average.
*Leaf orientation.*—Cascade downward from slightly arched petioles.
*Leaf color.*—Spring foliage, upper surface; 137A with very fine <1 mm) margin 144B, spring foliage lower surface; 189C, summer foliage upper surface; 137A, summer foliage lower surface; 189A covered with coating of 189C.
*Leaf size.*—Average of 35 cm in length, average of 17.5 cm in width when mature.
*Leaf quantity.*—About 3 to 4 per shoot (eye).
*Petiole size.*—Average of 38 cm in length, an average of 9 mm in width.
*Petiole color.*—Spring foliage: inner surface 144B with margins 137A, outer surface 145C with margins 137A, fall foliage; inner surface 144A with margins 137A, outer surface color between 145B and 145C with margins 137A.
*Petiole surface.*—Glabrous and slightly glaucous.
*Petiole shape.*—Sulcate.

Flower Scape Description:
*Scape shape.*—Round, solid.
*Scape number.*—One per mature eye under normal growing conditions.
*Scape posture.*—Arching.
*Scape size.*—Average of 76 cm in length and 4 mm in width.
*Scape color.*—144B.
*Scape surface.*—Glabrous and slightly glaucous.
*Leaf bracts.*—Average of 1 per scape, ovate in shape, apiculate apex, truncate base, glabrous on both surfaces, average of 3 cm in length and 2 cm in width, curved inward towards stem, color 146B to 146C blending with 145C towards base.

Flower Description:
*Inflorescence type.*—Terminal racemes of single bell-shaped flowers on elongated scapes.
*Lastingness of inflorescence.*—About 4 weeks from first opening bloom to fading of last opening bloom, individual blooms last about one day.
*Inflorescence height.*—About 76 cm.
*Inflorescence width.*—About 6.5 cm.
*Flower shape.*—Bell-shaped.
*Flower number.*—Average of 23 per scape.
*Flower internode length.*—Average of 1 cm.
*Flower fragrance.*—None detected.
*Flower bud shape.*—Spathulate.
*Flower bud size.*—About 5 cm in length and 1 cm in diameter.
*Flower bud color.*—Emerges with base 145C, middle region 76C to 76D and apex 85A, matures to base 145D suffused with 85C, middle region a blend of 85D and N155B and apex 85C.
*Flower size.*—About 5.5 cm in length and about 3 cm in diameter.
*Flower color.*—Blend of N155B, 85C and 85D.
*Pedicels.*—About 1.4 cm in length, 1.5 mm in diameter, color 145C suffused with 85D surface is glabrous and satiny.
*Perianth features.*—Comprised of 6 tepals, 3 interior and 3 exterior, overlapping in expanded region and fused in tube region.
*Tepal shape.*—Oblanceolate.
*Tepal size.*—About 4.5 cm in length, about 8 mm in width.
*Tepal color.*—Outer surface; blend of N155B and 85D with fine stripes of 85C, inner surface; blend of N155B and 85D with stripes of 85A.
*Tepal texture.*—Glabrous.
*Tepal margin.*—Entire.
*Tepal base.*—Fused.
*Tepal apex.*—Acute.
*Floral bracts.*—1 per flower, ovate in shape, apiculate apex, truncate base, glabrous on both surfaces, average of 2.5 cm in length and 1.4 cm in width, curved inward towards stem with apex reflexed, color of both surfaces 146B at apex blending towards base with 145D suffused lightly with 76D.

Reproductive Organs:
*Gynoecium.*—1 Pistil, style is about 5 cm in length, 1 mm in width and 145D in color, stigma is pilose and 145D in color, ovary is superior, compound, composed of 3 locules, oblong in shape, about 6 mm in length and 3 mm in width, and 145A in color.
*Androecium.*—6 stamens, filaments are 145D in color, 5.5 cm in length, 1 mm in width, recurved and extends about 1 cm beyond perianth, anthers are 3.5 mm in length, 1 mm in width, attachment is versatile, 202A in color, dehiscence is longitudinal, pollen is moderate in quantity and 146D in color.
*Fruit.*—Capsule; 3-chambered, about 2 cm in length, 4 mm in width, dries to a color between 164B and 165B.
*Seeds.*—6 to 10 developed seeds observed per capsule, about 6 mm in length and 3 mm in width, 202A in color.

It is claimed:

1. A new and distinct cultivar of *Hosta* plant named 'Neptune' as herein illustrated and described.

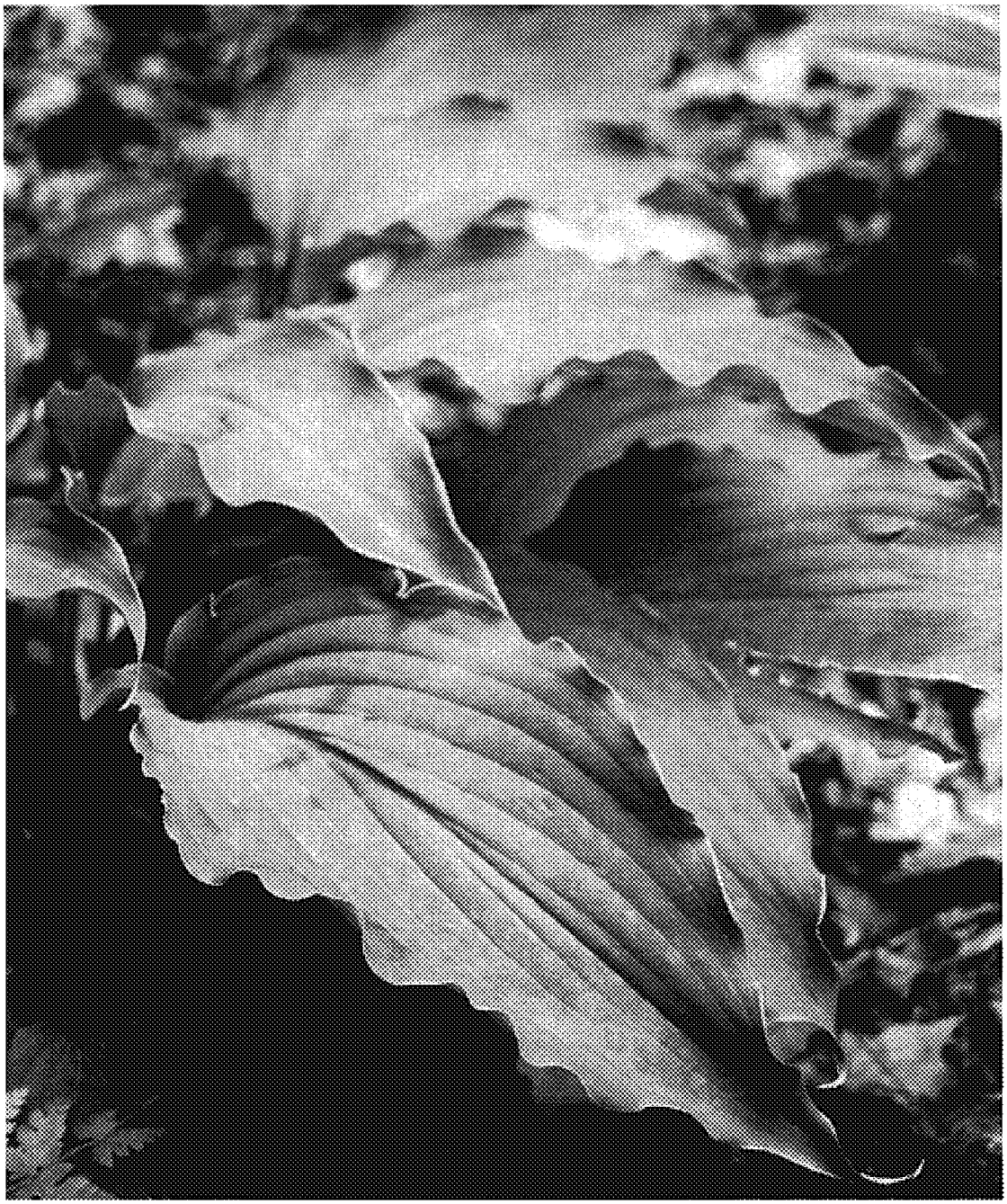

* * * * *